United States Patent [19]

Krause et al.

[11] Patent Number: 5,242,618
[45] Date of Patent: Sep. 7, 1993

[54] DI- AND TRIFLUOROTOLANS

[75] Inventors: Joachim Krause, Dieburg; Volker Reiffenrath, Rossdorf; Ulrich Finkenzeller, Plankstadt, all of Fed. Rep. of Germany

[73] Assignee: Merck Patent Gesellschaft, Darmstadt, Fed. Rep. of Germany

[21] Appl. No.: 688,125

[22] Filed: Apr. 19, 1991

[30] Foreign Application Priority Data

Apr. 19, 1990 [DE] Fed. Rep. of Germany ....... 4012403

[51] Int. Cl.$^5$ ..................... C09K 19/06; C07C 25/13; G02F 1/13
[52] U.S. Cl. ............................ 252/299.6; 252/299.01; 570/127; 570/129; 570/131
[58] Field of Search ........... 252/299.01, 299.6, 299.62, 252/299.65, 299.66; 570/127, 129, 131; 359/103

[56] References Cited

U.S. PATENT DOCUMENTS 4,839,091  6/1989  Goto et al. ..................... 252/299.63
5,032,313  7/1991  Goto et al. ..................... 252/299.63

FOREIGN PATENT DOCUMENTS 3906052   9/1989  Fed. Rep. of Germany .
61-260031 11/1986  Japan .
8802130   3/1988  World Int. Prop. O. .

Primary Examiner—Robert L. Stoll
Assistant Examiner—Shean C. Wu
Attorney, Agent, or Firm—Millen, White, Zelano, & Branigan

[57] ABSTRACT

Di- and trifluorotolans of the formula I.

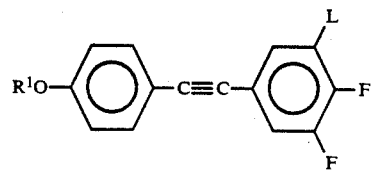

in which $R^1$ is alkyl having up to 9 carbon atoms, and

L is H or F are suitable as components of liquid-crystalline media.

9 Claims, No Drawings

DI- AND TRIFLUOROTOLANS

BACKGROUND OF THE INVENTION

The invention relates to di- and trifluorotolans of the formula I:

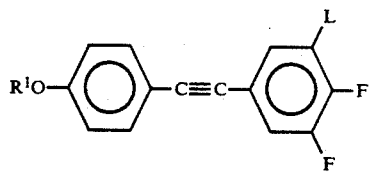

in which
R$^1$ is alkyl having up to 9 carbon atoms, and
L is H or F.

Compounds of the formula I can be used as components of liquid-crystalline media, in particular, for displays based on the principle of the twisted cell, the guest-host effect, the effect of deformation of aligned phases, or the effect of dynamic scattering.

Compounds of the formula I are also preferably suitable for use as components in liquid-crystalline media for highly twisted TN displays (for example, 180°-270°), i.e., for STN displays.

Similar compounds are known from JP 61/260031, but the compounds according to the invention have favorable nematic phase ranges compared with the substances described therein. See also copending Application Ser. No. 07/623,385, filed Nov. 19, 1990, and the priority applications upon which it is based, DE 39 29 525.7 and DE 39 29 526.5, both filed Sep. 6, 1985; DE 39 29 764.0, filed Sep. 7, 1989; and DE 40 09 907.5, filed Mar. 28, 1990. See also GB 8,922,168.3, filed Feb. 10, 1989.

SUMMARY OF THE INVENTION

An object of the invention is to provide novel, stable, liquid-crystalline or mesogenic compounds having relatively high birefringence which are suitable as components of liquid-crystalline phases. This object has been achieved by the provision of the compounds of the formula I.

It has been found that the compounds of the formula I are eminently suitable as components of liquid-crystalline media. They can be used, in particular, to prepare stable liquid-crystalline media having relatively high optical anisotropy and positive dielectric anisotropy. The substances of the formula I are particularly preferred, for example, for use in mixtures for STN displays.

Surprisingly, it has been shown that the addition of compounds of the formula I gives liquid-crystalline media which have a low temperature dependency of the threshold voltage, high electrical resistance, good miscibility with other liquid crystals and good low-temperature stability. In addition, the d/p window, which is important for STN displays, is positively affected.

In addition, the provision of the compounds of the formula I very generally considerably extends the range of liquid-crystalline substances which are suitable, from various applicational points of view, for the preparation of nematic mixtures.

DETAILED DESCRIPTION OF THE INVENTION

The compounds of the formula I have a broad range of applications. Depending on the choice of substituents, these compounds can be used as base materials from which liquid-crystalline media are predominantly composed; however, it is also possible to add compounds of the formula I to liquid-crystalline base materials from other classes of compounds in order for example, to optimize the dielectric and/or optical anisotropy of a medium of the dielectric and/or optical anisotropy of a medium of this type. The compounds of the formula I are furthermore suitable as intermediates for the preparation of other substances which can be used as constituents of liquid-crystalline media.

In the pure state, the compounds of the formula I are colorless and form liquid-crystalline mesophases in a temperature range which is favorably located for electrooptical use. They are very stable chemically thermally and to light.

The invention thus relates to the compounds of the formula I and to the use of these compounds as components of liquid-crystalline media. The invention furthermore relates to liquid-crystalline media containing at least one compound of the formula I, and to liquid-crystal displays which contain media of this type.

In the formula I, R$^1$ is an alkyl radical having up to 9 carbon atoms which may be straight-chain or branched. It is preferably straight-chain, has 2, 3, 4, 5, 6 or 7 carbon atoms and is accordingly preferably ethyl, propyl, butyl, pentyl, hexyl or heptyl, furthermore methyl, octyl or nonyl.

Compounds of the formula I having branched wing groups R may occasionally be of importance due to better solubility in the customary liquid-crystalline base materials, but in particular as chiral dopes if they are optically active.

Branched groups of this type generally contain not more than one chain branch. Preferred branched radicals are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl-, 2-propylpentyl, 2-octyl and 4-methylhexyl.

In the case of compounds containing branched wing groups, the formula I covers the optical antipodes and racemates and mixtures thereof.

The compounds of the formula I are prepared by methods known per se, as described in the literature (for example in the standard works such as Houben-Weyl, Methoden der Organischen Chemie [Methods of Organic Chemistry], Georg-Thieme-Verlag, Stuttgart), to be precise under reaction conditions which are known and are suitable for the reactions mentioned. Use may also be made here of variants which are known per se.

If desired, the starting materials can also be formed in situ by not isolating them from the reaction mixture, but instead reacting them further to form the compounds of the formula I.

Thus, the compounds of the formula I can be prepared by reacting appropriate p-substituted bromo- or iodobenzenes with the appropriate phenylacetylenes in the presence of a catalyst, such as, for example, bis(triphenylphosphine)palladium(II) chloride, or conversely by reacting p-alkoxyphenylacetylenes with the appropriate difluoro- or trifluoro-substituted bromo- or iodobenzenes.

The liquid-crystalline media according to the invention preferably contain 2 to 40, in particular 4 to 30, components as further constituents besides one or more compounds according to the invention. These media very particularly preferably contain 7 to 25 components besides one or more compounds according to the invention. These further constituents are preferably selected from nematic or nematogenic (monotropic or isotropic) substances, in particular substances from the classes of the azoxybenzenes, benzylideneanilines, biphenyls, terphenyls, phenyl or cyclohexyl benzoates, phenyl or cyclohexyl esters of of cyclohexylcyclohexanecarboxylic acid, cyclohexylphenyl esters of benzoic acid, of cyclohexanecarboxylic acid and of cyclohexylcyclohexanecarboxylic acid, phenylcyclohexanes, cyclohexylcyclohexanes, cyclohexylcyclohexylbenzenes, 4,4'-bis-cyclohexylbiphenyls, phenyl- or cyclohexylpyrimidines, phenyl- or cyclohexylpyridines, phenyl- or cyclohexyl-1,3-dithianes, 1,2-diphenylethanes, 1,2-dicyclohexylethanes, 1-phenyl-2-cyclohexylethanes, 1-cyclohexyl-2-(4-phenylcyclohexyl)ethanes, 1-cyclohexyl-2-biphenylethanes, 1-phenyl-2-cyclohexylphenylethanes, optionally halogenated stilbenes, benzyl phenyl ethers, tolans and substituted cinnamic acids. The 1,4-phenylene groups in these compounds may be fluorinated.

The most important compounds suitable as further constituents of media according to the invention can be characterized by the formulae 1, 2, 3, 4 and 5:

$$R'—L—E—R'' \quad 1$$

$$R'—L—COO—E—R'' \quad 2$$

$$R'—L—OOC—E—R'' \quad 3$$

$$R'—L—CH_2CH_2—E—R'' \quad 4$$

$$R'—L—C≡C—E—R'' \quad 5$$

In the formulae 1, 2, 3, 4 and 5, L and E, which may be identical or different, are in each case, independently of one another, a bivalent radical from the group formed by —Phe—, —Cyc—, —Phe—Phe—, —Phe—Cyc—, —Cyc—Cyc—, —Pyr—, —Dio—, —G—Phe— and —G—Cyc— and their mirror images, where Phe is unsubstituted or fluorine-substituted 1,4-phenylene, Cyc is trans-1,4-cyclohexylene or 1,4-cyclohexenylene, Pyr is pyrimidine-2,5-diyl or pyridine-2,5-diyl, Dio is 1,3-dioxane-2,5-diyl and G is 2-(trans-1,4-cyclohexyl)ethyl, pyrimidine-2,5-diyl, pyridine-2,5-diyl or 1,3-dioxane-2,5-diyl.

One of the radicals L and E is preferably Cyc, Phe or Pyr. E is preferably Cyc, Phe or Phe—Cyc. The media according to the invention preferably contain one or more components selected from the compounds of the formulae 1, 2, 3, 4 and 5 in which L and R are selected from the group comprising Cyc, Phe and Pyr and simultaneously one or more components selected from the compounds of the formulae 1, 2, 3, 4 and 5 in which one of the radicals L and E is selected from the group comprising Cyc, Phe and Pyr and the other radical is selected from the group comprising —Phe—Phe—, —Phe—Cyc—, —Cyc—Cyc—, —G—Phe— and —G—Cyc—, and optionally one or more compounds selected from the compounds of the formulae 1, 2, 3, 4 and 5 in which the radicals L and E are selected from the group comprising —Phe—Cyc—, —Cyc—Cyc—, —G—Phe— and —G—Cyc—.

In the compounds of the sub-formulae 1a, 2a, 3a, 4a and 5a, R' and R'' are in each case, independently of one another alkyl, alkenyl, alkoxy, alkenyloxy or alkanoyloxy having up to 8 carbon atoms. In most of these compounds, R' and R'' are different from one another, one of these radicals usually being alkyl or alkenyl. In the compounds of the sub-formulae 1b, 2b, 3b, 4b and 5b, R'' is —CN, —CF$_3$, —OCF$_3$, F, Cl, or —NCS; in this case, R has the meaning given for the compounds of the sub-formulae 1a to 5a and is preferably alkyl or alkenyl. However, other variants of the proposed substituents in the compounds of the formulae 1, 2, 3, 4 and 5 are common. Many such substances or alterna-tively mixtures thereof are commercially available. All these substances can be obtained by methods which are known from the literature or analogously thereto.

Besides components from the group comprising the compounds 1a, 2a, 3a, 4a and 5a (Group 1), the media according to the invention preferably also contain components from the group comprising the compounds 1b, 2b, 3b, 4b and 5b (Group 2), whose proportions are preferably as follows:

Group 1: 20 to 90%, in particular 30 to 90%,
Group 2: 10 to 80%, in particular 10 to 50%,
the sum of the proportions of the compounds according to the invention and of the compounds from Groups 1 and 2 adding up to 100%.

The media according to the invention preferably contain 1 to 40%, in particular preferably 5 to 30%, of compounds according to the invention. Further preferred media are those which contain more than 40%, in particular 45 to 90%, of compounds according to the invention. The media preferably contain three, four or five compounds according to the invention.

The media according to the invention are prepared in a manner which is customary per se. In general, the components are dissolved in one another, expediently at elevated temperature. By means of suitable additives, the liquid-crystalline phases can be modified in accordance with the invention in a manner such that they can be used in all types of liquid-crystal display elements which have hitherto been disclosed. Additives of this type are known to those skilled in the art and are described in detail in the literature (H. Kelker/R. Hatz. Handbook of Liquid Crystals, Verlag Chemie, Weinheim, 1980). For example, pleochroic dyes can be added for the production of colored guest-host systems, or substances can be added to modify the dielectric anisotropy, the viscosity and/or the orientation of the nematic phases.

The examples below are intended to illustrate the invention without representing a limitation. mp.=melting point, cp.=clear point. Above and below, percentages are percent by weight: all temperatures are indicated in degrees Celsius. "Customary work-up" means that water is added, the mixture is extracted with methylene chloride, and the organic phase is separated off, dried and evaporated, and the product is purified by crystallization and/or chromatography.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

In the foregoing and in the following examples, all temperatures are set forth uncorrected in degrees Celsius; and, unless otherwise indicated, all parts and percentages are by weight.

The entire disclosures of all applications, patents, and publications cited above and below and of corresponding German Application P 40 12 403.7, filed Apr. 19, 1990, is hereby incorporated by reference.

In addition, the abbreviations have the following meanings:

C: crystalline-solid state. S: smectic phase (the index characterizes the phase type). N: nematic state. Ch: cholesteric phase. I: isotropic phase. The number between two symbols indicates the conversion temperature in degrees Celsius.

In the present application and in the examples below, the structures of the liquid-crystal compounds are indicated by acronyms, the transformation into chemical formulae taking place as in Tables A and B below. All the radicals $C_nH_{2n-1}$ and $C_mH_{2m-1}$ are straight-chain alkyl radicals containing n or m carbon atoms. The coding in Table B requires no further explanation. In Table A, only the acronym for the parent structure is given. In individual cases, a code follows for the subsitutent $R^1$, $R^2$, $L^1$ and $L^2$, separated from the acronym for the parent structure by a hyphen:

| Code for $R^1$, $R^2$, $L^1$, $L^2$ | $R^1$ | $R^2$ | $L^1$ | $L^2$ |
|---|---|---|---|---|
| nm | $C_nH_{2n+1}$ | $C_mH_{2m+1}$ | H | H |
| nOm | $C_nH_{2n+1}$ | $OC_mH_{2m+1}$ | H | H |
| nO.m | $OC_nH_{2n+1}$ | $C_mH_{2m+1}$ | H | H |
| n | $C_nH_{2n+1}$ | CN | H | H |
| nN.F | $C_nH_{2n+1}$ | CN | H | F |
| nF | $C_nH_{2n+1}$ | F | H | H |
| nOF | $OC_nH_{2n+1}$ | F | H | H |
| nCl | $C_nH_{2n+1}$ | Cl | H | H |
| nF.F | $C_nH_{2n+1}$ | F | H | F |
| nOmFF | $C_nH_{2n+1}$ | $OC_mH_{2m+1}$ | F | F |
| nmF | $C_nH_{2n+1}$ | $C_mH_{2m+1}$ | F | H |
| nCF$_3$ | $C_nH_{2n+1}$ | CF$_3$ | H | H |
| nOCF$_3$ | $C_nH_{2n+1}$ | OCF$_3$ | H | H |
| nOCF$_2$ | $C_nH_{2n+1}$ | OCHF$_2$ | H | H |
| nS | $C_nH_{2n+1}$ | NCS | H | H |
| rVsN | $C_rH_{2r+1}$—CH=CH—$C_sH_{2s}$— | CN | H | H |
| rEsN | $C_rH_{2r+1}$—O—$C_sH_{2s}$— | CN | H | H |
| nNF | $C_nH_{2n+1}$ | CN | F | H |
| nAM | $C_nH_{2n+1}$ | COOC$_m$H$_{2m+1}$ | H | H |
| nOF.F | $OC_nH_{2n+1}$ | F | H | F |

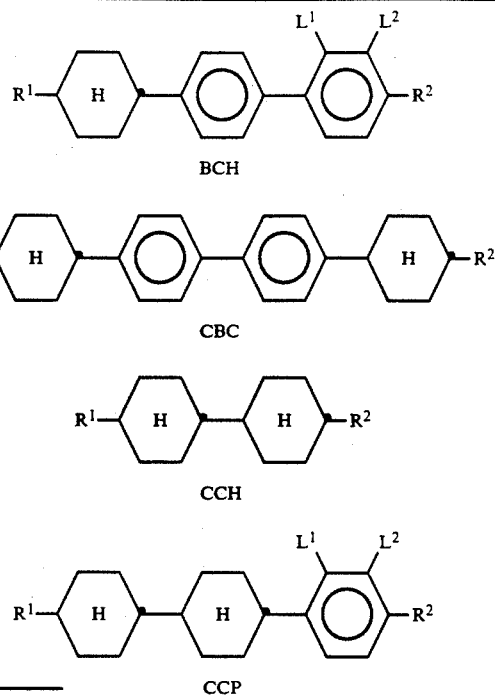

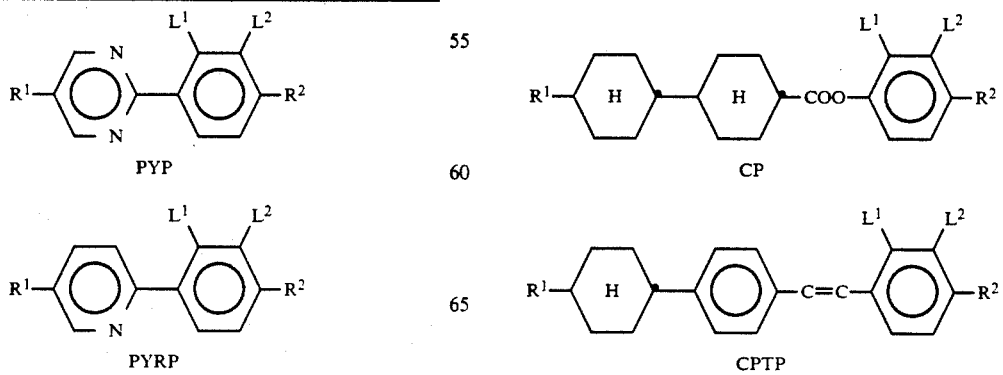

TABLE A-continued
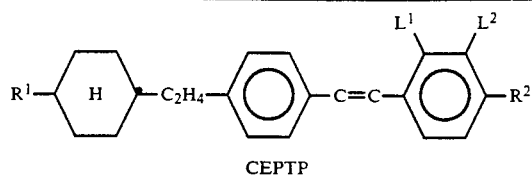
CEPTP
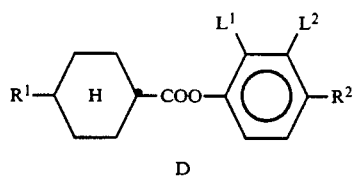
D
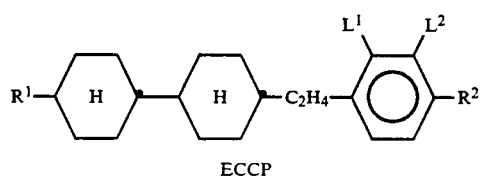
ECCP
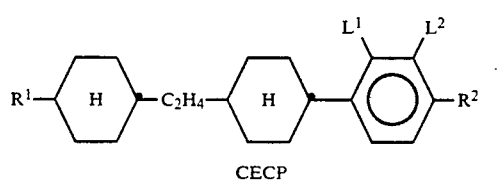
CECP
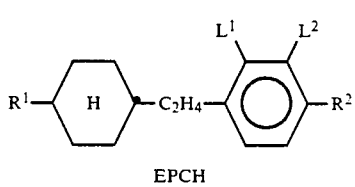
EPCH
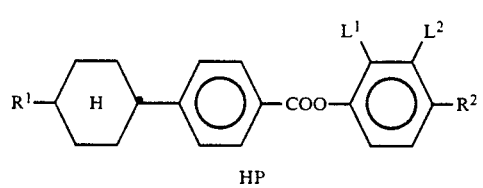
HP
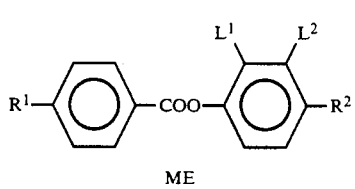
ME
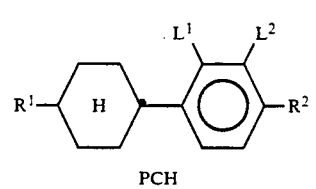
PCH
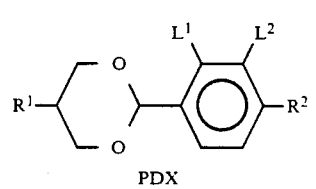
PDX
TABLE A-continued
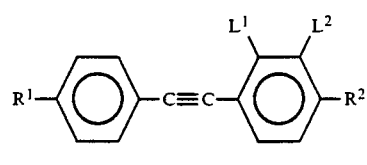
PTP
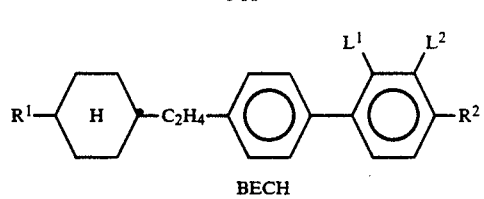
BECH
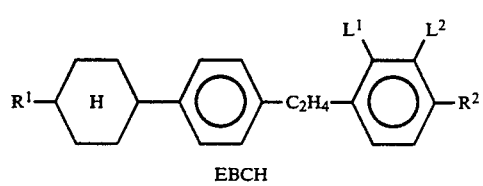
EBCH
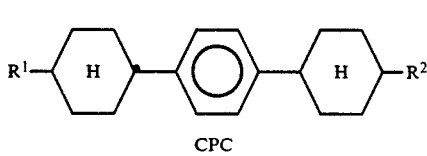
CPC
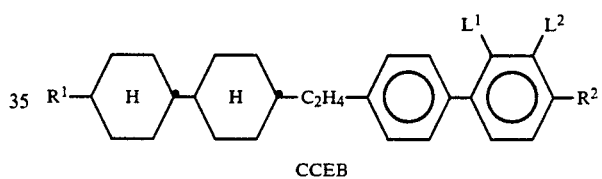
CCEB
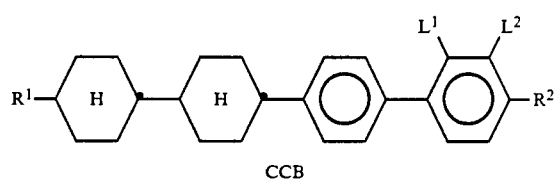
CCB
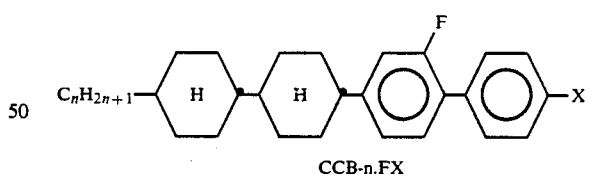
CCB-n.FX
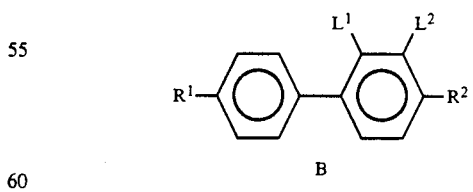
B
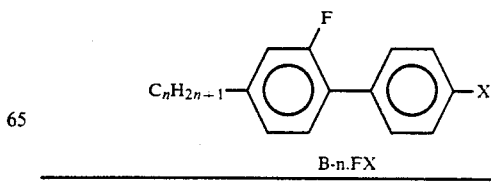
B-n.FX TABLE B
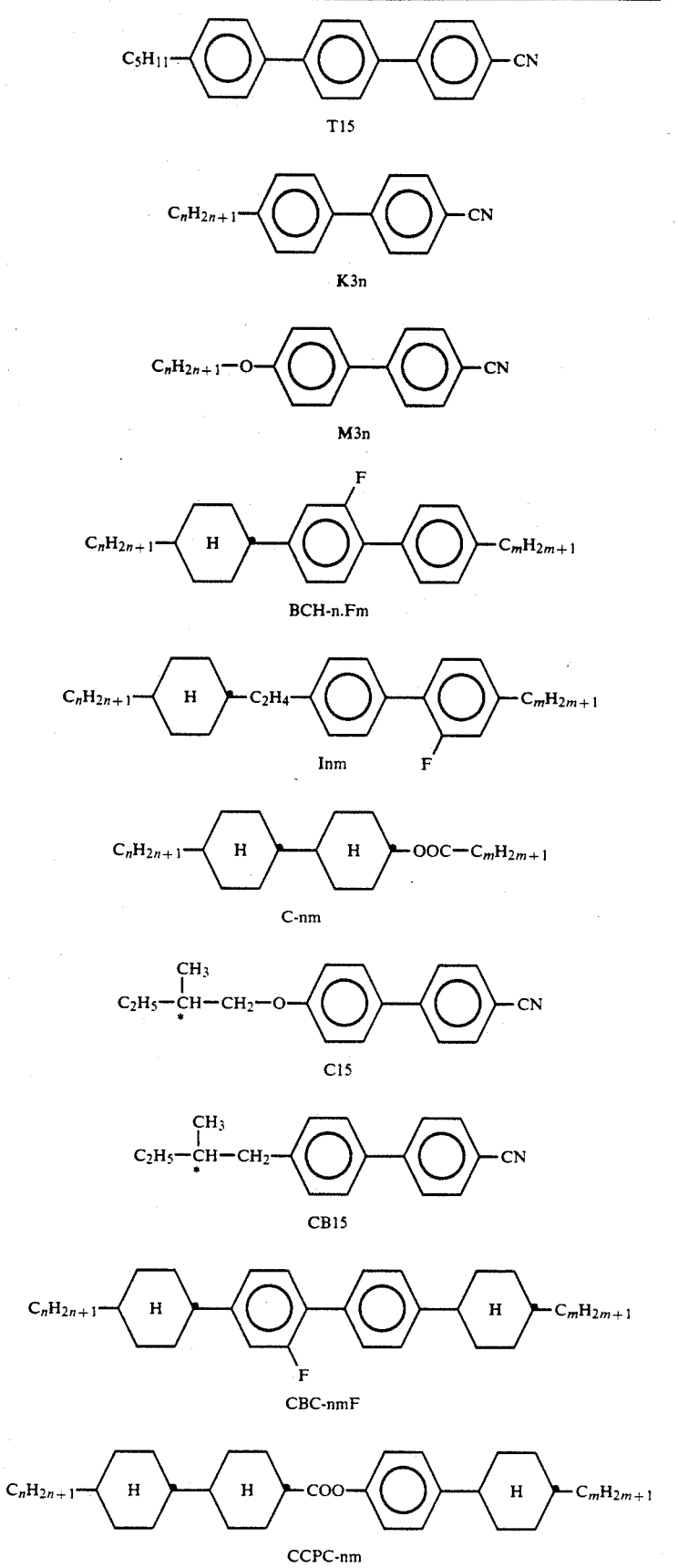

TABLE B-continued
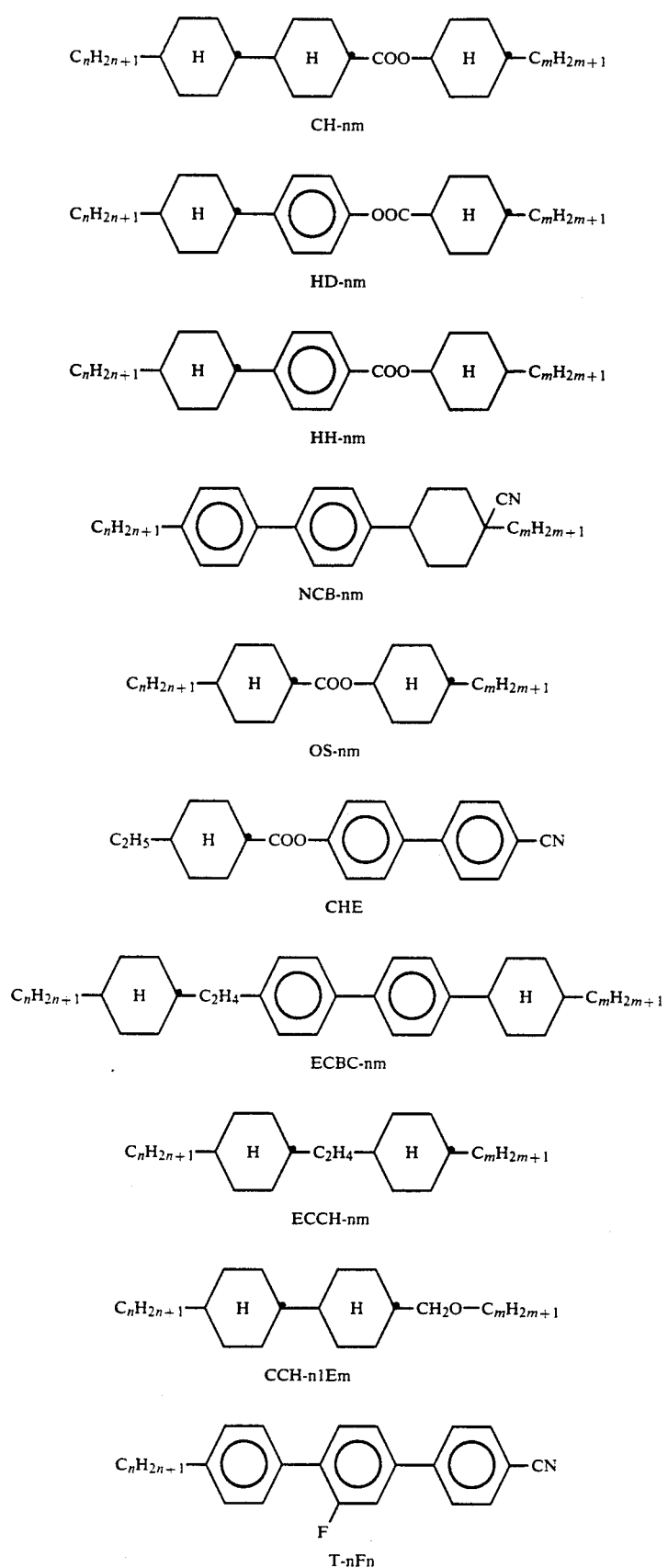

TABLE B-continued

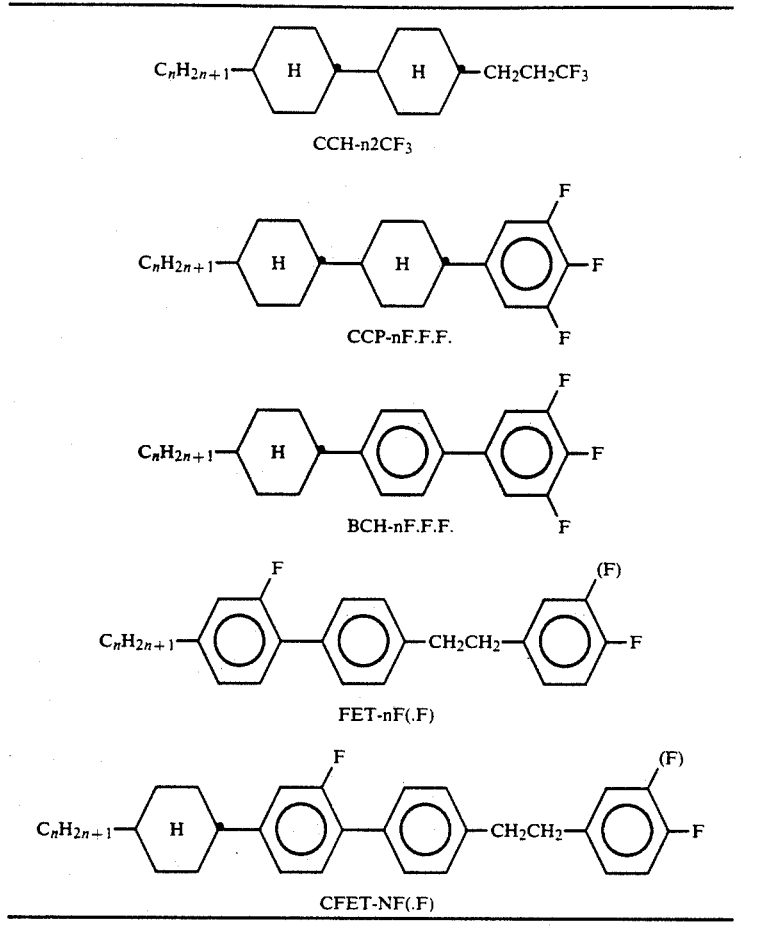

EXAMPLE 1

0.4 mmol of bis(triphenylphosphine)palladium(II) chloride and 0.2 mmol of CuI are added at room temperature to a mixture of 0.02 m of 4-ethoxyphenylacetylene, 0.02 m of 3,4-difluoroiodobenzene and 50 ml of triethylamine. The reaction mixture is stirred at room temperature for 2 hours, diluted with 100 ml of methyl tert.-butyl ether and filtered with suction, and the solution is evaporated. Purification by chromatography and/or crystallization gives 3,4-difluoro-4'-ethoxytolan, K 67 I, $\Delta\epsilon = 11.18$.

The following are prepared analogously:
3,4-difluoro-4'-methoxytolan
3,4-difluoro-4'-propoxytolan
3,4-difluoro-4'-butoxytolan
3,4-difluoro-4'-pentoxytolan
3,4-difluoro-4'-hexoxytolan
3,4-difluoro-4'-heptyloxytolan
3,4-difluoro-4'-octyloxytolan
3,4-difluoro-4'-nonyloxytolan

EXAMPLE 2

0.4 mmol of bis(triphenylphosphine)palladium(II) chloride and 0.2 mmol of CuI are added at room temperature to a mixture of 0.02 m of 4-butoxyphenylacetylene, 0.02 m of 3,4,5-trifluorobromobenzene and 50 ml of triethylamine. The reaction mixture is stirred at room temperature for 2 hours, diluted with methyl tert.-butyl ether and filtered with suction, and the solution is evaporated. Purification by chromatography and/or crystallization gives 3,4,5-trifluoro-4'-butoxytolan.

The following are prepared analogously:
3,4,5-trifluoro-4'-methoxytolan
3,4,5-trifluoro-4'-ethoxytolan
3,4,5-trifluoro-4'-propoxytolan
3,4,5-trifluoro-4'-butoxytolan
3,4,5-trifluoro-4'-pentoxytolan
3,4,5-trifluoro-4'-hexoxytolan
3,4,5-trifluoro-4'-heptyloxytolan
3,4,5-trifluoro-4'-octyloxytolan
3,4,5-trifluoro-4'-nonyloxytolan

EXAMPLE A

A liquid-crystalline medium is obtained containing

| | |
|---|---|
| 9.0% | PCH-5F |
| 7.2% | PCH-6F |
| 5.4% | PCH-7F |
| 7.2% | CCP-20CF$_3$ |
| 10.8% | CCP-30CF$_3$ |
| 8.1% | CCP-40CF$_3$ |
| 8.1% | CCP-50CF$_3$ |
| 10.0% | PTP-20F.F |
| 4.5% | ECCP-30CF$_3$ |
| 4.5% | ECCP-50CF$_3$ |
| 1.8% | CBC-33F |
| 1.8% | CBC-53F |
| 1.8% | CBC-55F | and exhibits $T_c = 83.8°$ C., $\Delta\epsilon = 5.8$, $\Delta n = +0.113$ and $V_{20°\ C.} = 14$ mm$^2$/s.

What is claimed is:

1. Difluorotolans of the formula I

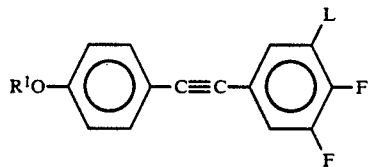

in which
R¹ is alkyl having up to 9 carbon atoms, and
L is H.

2. Difluorotolans according to claim 1, in which R¹ is ethyl, propyl, or pentyl.

3. A method of preparing liquid-crystalline media, the improvement which comprises adding the compounds of the formula I according to claim 1 as components of the liquid-crystalline media.

4. A liquid-crystalline media having at least two liquid-crystalline components, characterized in that it contains at least one compound of the formula I according to claim 1.

5. A liquid-crystal display, characterized in that it contains a liquid-crystalline medium according to claim 4.

6. Each of the compounds:
3,4-difluoro-4'-methoxytolan;
3,4-difluoro-4'-ethoxytolan;
3,4-difluoro-4'-propoxytolan;
3,4-difluoro-4'-butoxytolan;
3,4-difluoro-4'-pentoxytolan;
3,4-difluoro-4'-hexoxytolan;
3,4-difluoro-4'-heptyloxytolan;
3,4-difluoro-4'-octyloxytolan; and
3,4-difluoro-4'-nonyloxytolan according to claim 1.

7. A liquid crystal medium as in claim 4 having from 1-40% of compounds of formula I.

8. A liquid crystal medium as in claim 4 having from 45-95% of compounds of formula I.

9. A liquid crystal medium as in claim 4 which contains from 3-5 different compounds of formula I.

* * * * *